United States Patent [19]

Karnis

[11] 4,253,329
[45] Mar. 3, 1981

[54] FIBRE FLEXIBILITY METER

[75] Inventor: Alkibiadis Karnis, Dollard des Ormeaux, Canada

[73] Assignee: Domtar Inc., Montreal, Canada

[21] Appl. No.: 92,655

[22] Filed: Nov. 9, 1979

[51] Int. Cl.³ .................................................. G01N 33/00
[52] U.S. Cl. .................................................. 73/63; 162/49
[58] Field of Search .................. 73/63; 162/49, 198, 162/263

[56] References Cited

U.S. PATENT DOCUMENTS

| 3,873,416 | 3/1975 | Forgacs et al. ............. | 73/63 X |
| 3,893,334 | 7/1975 | Williams ..................... | 73/63 X |

OTHER PUBLICATIONS

Hill, J. et al., *Evaluations of Screens by Optical Measurements,* In Tappi, 58(10), Oct. 1975, pp. 120–124.
Proceedings, *International Mechanical Pulping Conf. 1973,* Stockholm, Swe., Jun. 1973, pp. 1–23.

*Primary Examiner*—Gerald Goldberg
*Assistant Examiner*—Joseph W. Roskos

[57] ABSTRACT

A method and apparatus are disclosed for obtaining an indication of fibre flexibility by spraying a pulp sample of preselected average fibre length against the bottom of a horizontal screen having a negative pressure thereabove whereby a selected pressure drop is applied across the screen and the pulp sample is divided into a retained and a passed fraction. The flexibility index is obtained by a ratio indicative of the fibre mass in the passed fraction or retained fraction to the fibre mass in the feed.

8 Claims, 11 Drawing Figures

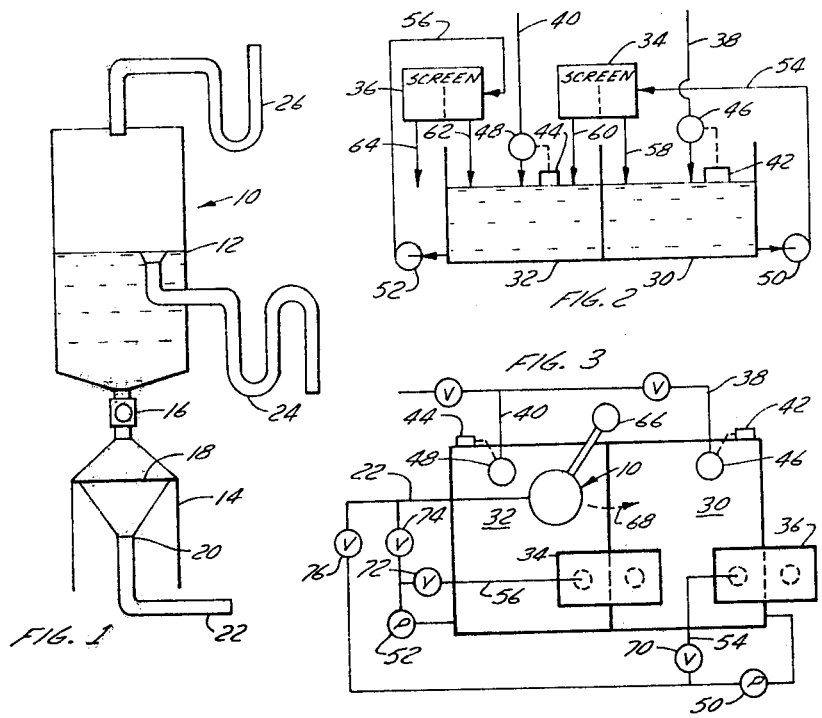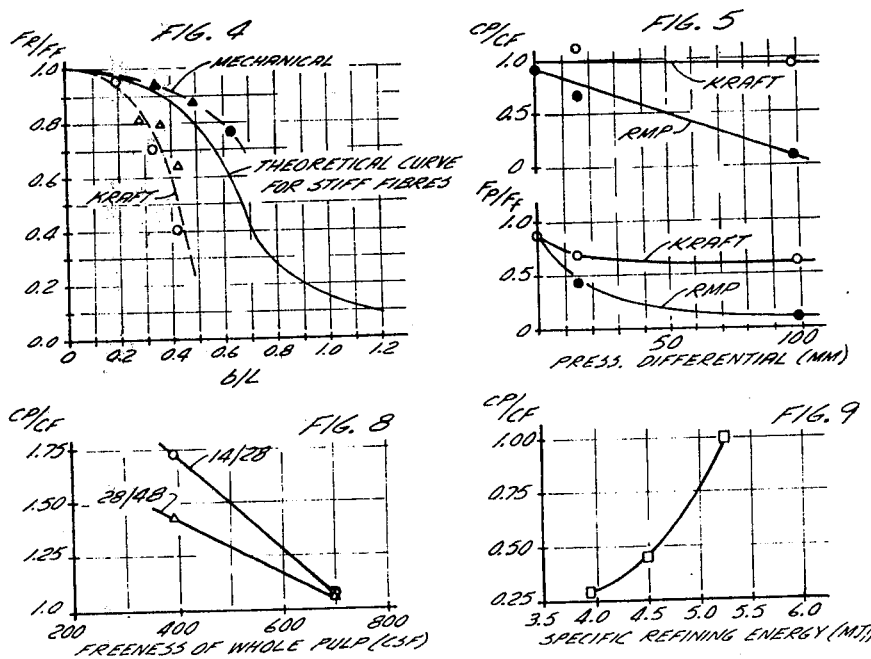

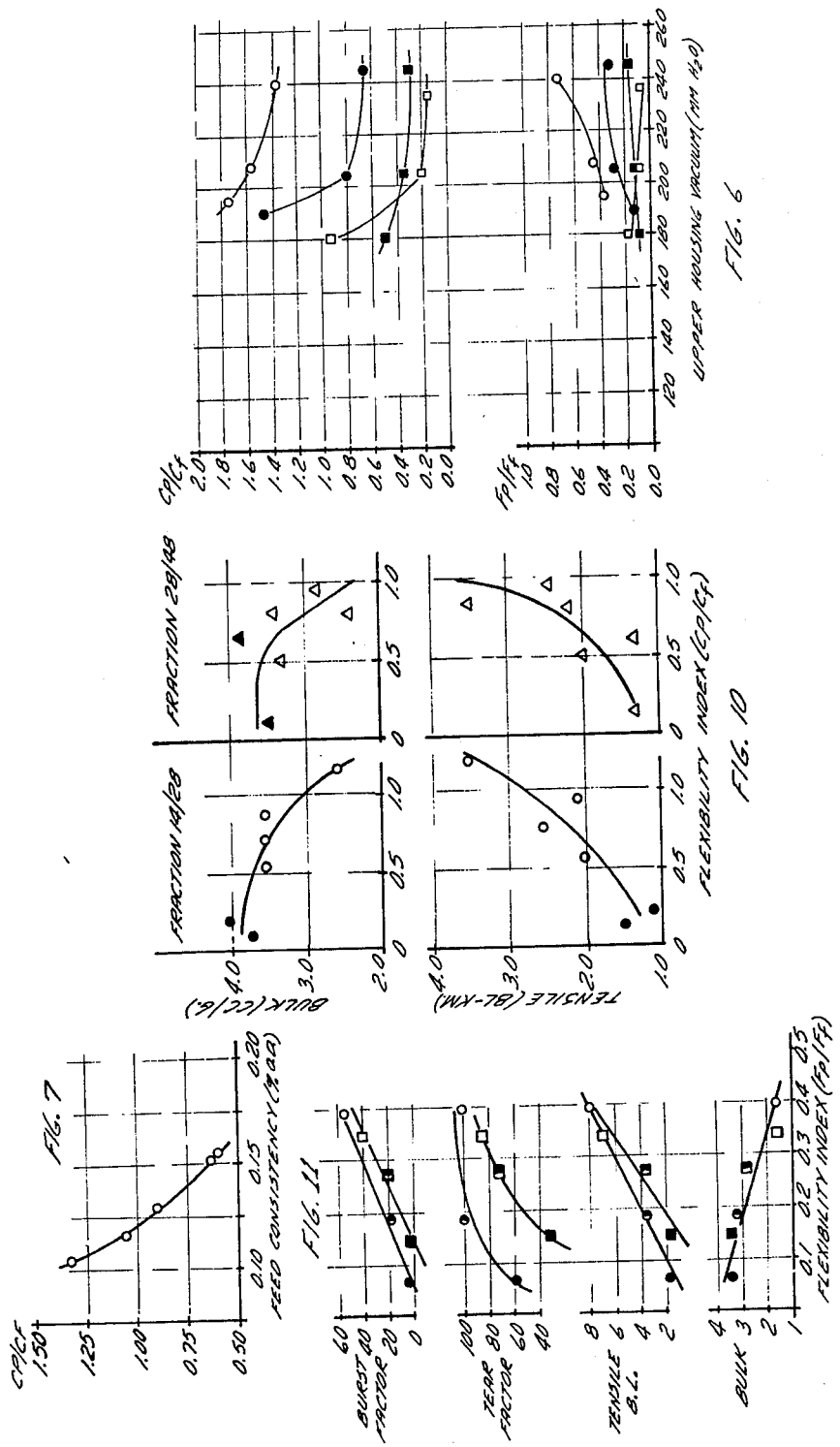

4,253,329

FIBRE FLEXIBILITY METER

FIELD OF THE INVENTION

The present invention relates to a device for determining fibre flexibility. More particularly the present invention relates to a device for indicating the fibre flexibility of wood pulps.

BACKGROUND OF THE INVENTION

The flexibility property of fibres used in papermaking is important, particularly for the low yield chemical pulps, high yield semi-chemical and chemi-mechanical pulps as it contributes significantly to, amongst other things, the bonding properties of the pulp.

Fibre flexibility is extremely difficult to measure using conventional techniques, but, it can and has been measured on a single fibre basis in the laboratory using laborious methods that are both time consuming and subjective. Two such techniques are reviewed in an article on cellulose fibre bonding by Ulla-Britt Mohlin in Svensk Papperstidning No 11 1975 page 412. There are no techniques available for determining fibre flexibility based on significant size samples, nor is there any equipment known that provides a relative and nonsubjective indication of flexibility.

BROAD DESCRIPTION OF THE INVENTION

It is thus the object of the present invention to provide a method and apparatus to measure fibre flexibility of a pulp sample that may be relatively quickly operated and is adaptable to on-line monitoring of fibre flexibility.

Broadly the present invention comprises a method and apparatus for measuring fibre flexibility wherein a slurry of such fibres is first screened to obtain a fraction of a selected average fibre length and then the fraction of selected average fibre length at a suitable preselected consistency is sprayed against the bottom of a substantially horizontal screen having a pool of liquid maintained there above by the application of suction to the area above the screen and measuring at least one of a passed fraction or a retained fraction from such screen to obtain an indication of the fibre split by this screen and thereby obtain an indication of the degree of flexibility.

Further features, objects and advantages will be evident from the following detailed description of the preferred embodiments of the present invention taken in conjunction with the accompanying drawings in which:

FIG. 1 is a schematic representation of the screening equipment to measure fibre flexibility.

FIG. 2 is a schematic representation of one means for obtaining a fibre fraction of preselected average fibre length.

FIG. 3 is a schematic planned view of flexiblity meter of the present invention incorporating means for obtaining preselected fibre length fraction and the device for screening.

FIG. 4 is a plot of the ratio of fibres in the retained fraction ($F_r$) to the fibres in the feed ($F_f$) vs a ratio of the size of screen opening to the fibre length to be tested.

FIG. 5 is a plot of consistency ratio ($C_p/C_f$) and fibre ratio ($F_p/F_f$) of the pass fraction to the feed vs the pressure differential across the screen.

FIG. 6 is a plot of consistency ratio ($C_p/C_f$) and fibre ratio ($F_p/F_f$) of the passed fraction to the feed vs the vacuum in the upper housing in mm of water.

FIG. 7 is a plot of the ratio of pass fraction to feed fraction consistencies ($C_p/C_f$) vs the feed consistency ($C_f$) as percent oven dried at a pressure drop across the screen of 15 mm $H_2O$.

FIG. 8 is a plot of flexibility index ($C_p/C_f$) vs freeness of the whole pulp in Canadian standard freeness for two different fractions of a bleached softwood kraft.

FIG. 9 is a plot of flexibility index ($C_p/C_f$) vs specific refining energy for a refiner softwood pulp retained on the 35 mesh screen.

FIG. 10 is a plot of bulk and tensile for the passed 14 retained 28 fraction and passed 28 retained 48 fraction vs flexibility index ($C_p/C_f$), and FIG. 11 is a plot of burst factor, tear factor, tensile and bulk vs flexibility index ($F_p/F_f$) for different fractions of a thermomechanical pulp, a 50—50 mixture of thermomechanical pulp and kraft pulp and for kraft pulp.

Referring now to FIG. 1, generally as indicated schematically in FIG. 1, the fibre flexibility meter 10 is formed by a device having an upper housing 12 connected to a lower housing 14 by a quick opening valve 16. The lower housing 14 spaced from its upper end is traversed by a horizontal screen 18, and spaced below this screen is a nozzle 20 adapted to direct a slurry of pulp fibres against the bottom of screen 20. Pulp fibre slurry is fed to the nozzle 20 via a pipe 22.

The upper chamber 12 has an overflow pipe 24 for extraction of the sample to be tested or to be measured and a connection to a vacuum pump or the like as indicated by line 26. In this device the pulp sample is introduced via line 22 and sprayed via the nozzle 20 against the bottom of the screen 18. Negative pressure is maintained above the screen 18 by having the valve 16 opened so that the upper portion of housing 14 above the screen 18 is subjected to the vacuum applied via the line 26. The pulp fraction after passing through the screen 18 passes through the quick opening valve 16 into the upper chamber 12 and is withdrawn via line 24. The valve 16 is only necessary to facilitate the information of the negative pressure above the screen 18 and to close off the apparatus.

The fibre length of the fraction fed to the flexibility meter 10 must be reasonably controlled to ensure sensitivity and reproducibility of the results generated by the meter. The fibre fraction to be fed via line 22 may be obtained from a fibre length classifier such as a Bauer-McNett Classifier or alternatively in the preferred embodiment of the present invention, screening means will be provided in the meter itself.

Such a means is shown in FIG. 2 and in the illustrated arrangement is composed of two tanks 30 and 32 and two screens 34 and 36. These screens are vertical self cleaning screens. Dilution water is added to the two tanks 30 and 32 via lines 38 and 40, with the flows of dilution water being controlled by sensors 42 and 44 respectively sensing the level of the tanks 30 and 32 and controlling the valves 46 and 48 respectively in the lines 38 and 40. Pumps 50 and 52 pump the samples in tanks 30 or 32 respectively through lines 54 or 56 to the screens 34 and 36 respectively. The rejects from the screen 34 pass via line 58 back to the tank 30 and the accepts pass via line 60 into the tank 32 while the rejects from screen 36 pass via line 62 to the tank 32 and the accepts pass via line 64 to be disposed of.

To obtain samples of the required fibre length for feeding to the flexibility meter of FIG. 1, a sufficiently large sample is placed in the tank 30 and is pumped via pump 50 and line 54 to the screen 34 where it is separated by a screen which may be suitably selected to give a fraction equivalent to say a 28 mesh screen of a Bauer-McNett Classifier, so that the material passing through the screen 34 and entering tank 32 would be the pass 28 portion of the sample while the rejects are simply returned to the tank 30 and represent the long fibre fraction (retained 28) and are recirculated. It is apparent that the level in the tank 30 decreases and it is necessary then to add water via line 38, to maintain the level substantially constant whereby the consistency in the tank 30 obviously diminishes.

The accepts accumulating in the tank 32 are pumped via pump 52 and line 56 to the screen 38 which could be equivalent, for example, to say a 48 mesh screen of a Bauer-McNett Classifier. The material retained thereon (the rejects) would pass via line 62 back to the tank 32, whereby the tank 32 will accumulate a fraction of pass 28 retained 48 (or whatever other fraction desired).

The consistency in the tank 32 is changing since material is being removed via line 64 and water is added by a line 40 to maintain a constant level in the tank. Before testing in the flexibility meter the consistency of the pulp fractions in the tanks 30 and 32 is adjusted to say 0.15%, by either adding dilution water if it is too high, or shutting off the dilution valve and running the pulp through the screen if too low.

As shown in FIG. 3, which is a schematic plan view of the combination of the flexibility meter of FIG. 1 and the fractionator of FIG. 2, it will be noted that the meter 10 is mounted on a pedestal 66 and is movable back and forth from a position overlying the tank 32 to a position overlying the tank 30 as indicated by the arrow 68.

After stable operation of the fractionator has been obtained (after a predetermined period of time sufficient to form a selected length fraction in tank 32) the valves 70 and 72 in the lines 54 and 56 (see FIG. 3) are closed and the pumps 50 and 52 are stopped. If the flexibility of the pulp fraction in the tank 32 is to be tested, the consistency is adjusted as above described to the consistency designated for testing and the valve 74 is opened and the pump 52 operated to pump stock from the tank 32 through valve 74 and lines 22 to the flexibility meter 10 i.e. to the nozzle 20. Stock passing through the screen of the flexibility meter will pass into the tank 12 (FIG. 1) whereas the rejects will fall back into the tank 32.

If it is desired to test the flexibility of the sample in the tank 30, the consistency in this tank is adjusted as required, the flexibility meter 10 is moved as indicated by the arrow 68 to overlay the tank 30, valve 74 is closed and valve 76 opened, pump 50 is operated to pump via valve 76 and line 22 to the flexibility meter 10.

The operation of the horizontal screen for determining flexibility is affected by the variables in the pulp fibres themselves and the operating variables of the equipment.

The most important or most significant fibre variables are fibre length and fibre flexibility. To eliminate as far as possible the effect of fibre length on the determination of flexibility, the pulp sample is first screened to obtain a fraction of a preselected fibre length, say the pass 14 retained 28 mesh fraction of a Bauer-McNett fibre classifier (or any other suitable fibre length fraction).

The operating variables of the process or equipment should be maintained substantially the same for each test.

One of the main operating variables is the size of screen openings of the flexibility meter which must be correlated with the fibre length of the fraction to be tested i.e. the openings must be smaller than the average fibre length of the pulps being tested and yet have a significantly high pass through for the more flexible fibres. In practice it has been found that the passed 14 retained 28 fibre length fraction of the Bauer-McNett, for softwood pulps, preferably should be tested with a 16 mesh screen and for the passed 28 retained 48 fraction with a 30 mesh screen.

More adequately to describe the requirements of mesh size, reference may be made to FIG. 4 which is a plot of $F_r/F_f$ (amount of fibre in the retained fraction/amount of fibre in the feed) vs b/L where b is the length of one side of the square opening in the screen of the flexibility meter and L is a fibre length of the feed. In order to get a significant difference in the ratio $F_r/F_f$ it is necessary that the ratio b/L be in the range of approximately 0.3 to about 0.7. Preferably operation will be at about 0.5 to 0.6 range which means that the dimension b of the screen should normally be about ½ of the fibre length of the material being tested. The dimension b has been described for a screen opening that is square but equivalent values for other shapes openings e.g. rectangular, etc., may be determined. The paper by Ronald Estridge in TAPPI April 1962 Vol. 45 No. 4 provides a theoretical mode of obtaining equivalent values or they may be determined empirically.

In FIG. 4, the open circles represent a kraft pulp and the closed or filled circles indicate a mechanical pulp of the passed 14 retained 28 fraction, while the opened triangles represent kraft and the closed triangles mechanical pulps of the passed 28 retained 48 fraction. The centre curve is the theoretical curve for stiff fibres as derived in the above by Estridge for paper machine wire drainage or screen operation.

Another parameter is the pressure differential across the screen 18 of the flexibility meter since this has a very significant effect on fibre split. This pressure differential should not be so strong as to build up a mat of fibres on the bottom of the screen (especially with stiff fibres) which would significantly influence the operation of the screen and interfere with the passage of a fraction therethrough. This relationship is clearly indicated in FIG. 5. The open circles represent a kraft pulp and closed circles a refiner mechanical pulp (RMP); $C_p/C_f$ is the ratio of passed fraction consistency to feed consistency, and $F_p/F_f$ is the fibre mass flow in the passed fraction to fibre mass flow in the feed. It is apparent that to obtain discrimination between flexible kraft fibres and mechanical fibres, a pressure differential across the screen must be maintained, however care must be taken to insure that the pressure drop is not so high that a mat is formed on the screen yet sufficiently high to place a bending force on the fibres. The permissible range of pressure drop will vary depending on the stiffness and/or type of fibres being tested and will generally be in the range of 10 to 150 mm of water, however preferably this will be the same for all tests and will be in the range of 20-25 mm of water.

The build-up of fibres on the screen 18 is in part determined by the flow rate through the screen which, in itself, is determined in part by the negative pressure maintained in the upper housing 12. Obviously, this negative pressure must at least be sufficient to maintain a flow into the housing 18 and out through the overflow 24 and should be at least sufficient to obtain a stable operation, as will be well apparent from the discussion of FIG. 6.

In FIG. 6, the opened designations are for the passed 14 retained 28 fraction and the closed designations are for the passed 28 retained 48 fraction. The circles designate softwood kraft and the squares thermomechanical pulps.

It will be apparent that until a flow is established, there can be no reading of either $C_p$ or $F_p$, thus it is essential that the samples be accumulated. If the flow rate is too low, the proportion of fibres to water flowing out of the upper housing 12 may be effected as will be apparent from the left hand portions of the curves of $C_p/C_f$ vs pressure in mm $H_2O$. The consistency of the passed fraction flowing from the upper chamber 12 at low vacuum is significantly higher than when the flow rate increases, thereby indicating a preferential flow of fibres to water at low vacuum. It will be noted that the consistency of the passed fraction ($C_p$) seems to stabilize at a lower value and to change very little after a certain minimum of flow rate has been obtained. For this reason, it is preferred to operate in what is designated herein as the "stabilized" region which is indicated by that portion of the curve with a relatively slight slope and for the specific instrument used is obtained with a negative pressure in the upper housing of about 200 inches of water or slightly over. There is little point in increasing the vacuum significantly beyond this region, since such an increase will do nothing to clarify the results and if the vacuum is increased too much the pressure drop across the screen 18 may be increased to a point where a mat is forming thereby disrupting the operation of the equipment.

It will be noted that both the consistency of the passed fraction and the mass flow of the passed fraction tend to stabilize in the "stabilized" region. However, the mass flow is significantly influenced by the amount of water travelling with the fibres in the passed fraction and reduces scale of the differences that can be discriminated between various pulps. It is preferred to use the ratio of either the consistency of the retained fraction of the passed fraction to the consistency of feed to designate flexibility. Obviously, it is very easy to obtain a sample of the passed fraction therefore the ratio of the consistency of the passed fraction to the feed fraction i.e. $C_p/C_f$ is preferred. The selection of the consistency rather than the mass flow ratio ($F_p/F_f$) also simplifies the equipment and tests necessary to obtain the required information.

The nozzle 20 should be designed to project the fibres against the screen in a consistent manner. This is obtained for example by a random distribution of the fibre orientation as they strike the screen. Also the through put rate should be set for all tests, since, if the through put rate is changed the velocity of the fibres at impact is changed. At lower throughput rates, the ratio of fibres passing through the screen to those retained decreases, for example, at the feed rate of 21.5 l/min the ratio of fibres pass the screen to fibres fed to the screen is 0.75, whereas, when the flow rate to the screen was reduced to 11 l/min, this ratio for the same fibres decreased to 0.3.

Another important variable is feed consistency, as will be apparent from FIG. 7 which shows the change in the consistency ratio of the passed fraction to that of the feed as a function of feed consistency for a mechanical pulp. If the feed consistency changes, so does the consistency ratio and thus, since the consistency ratio is the indicator (as well as the fibre ratio or quantity ratio) of the flexibility meter, it is important that the consistency of feed to the meter be maintained substantially constant in the range of 0.05-0.3. It is preferred to operate with a consistency of about 0.15%.

Laboratory equipment may conveniently have the area of screen 18 equivalent to about a 4" diameter. Obviously for consistently meaningful results, the nozzle 20 must be of a preset design which is in the preferred arrangement is a full cone nozzle and the channels must be large enough to allow the pass of the larger size particles expected to be found in the slurry. The spray is directed to spray substantially uniformly over the whole area of the screen 18 with a random orientation of the fibres as they strike the screen 18.

The preferred conditions of operation are at a feed consistency of about 0.15% using a screen 18 with a b/L ratio equivalent to between 0.5 and 0.6, for a screen with square openings a pressure drop across the screen of between 20 and 25 mm of water, a substantially constant vacuum in upper chamber 12 of 200 or more for the specific equipment used and preferably in the "stabilized" flow regions and the nozzle 20 spraying over an area of about 4 inches diameter on the screen 18 with a random orientation to the fibres as they reach the screen 18. The screens 34 and 36 are preferably of mesh size 16 and 30 respectively.

The following examples will illustrate the effectiveness of the present invention in discriminating pulps on the basis of fibre flexibility.

EXAMPLE 1

The preferred embodiment of the apparatus was used to test the same fractions of different types of pulps. Table I shows the differences found with respect to yield and pulping processes. Fibre flexibility is known to decrease with increasing yield and it is generally higher for sulphite than sulphate pulps.

TABLE 1

| PULP | YIELD % | Flexibility Index ($C_p/C_f$) | |
|---|---|---|---|
| | | 14/28 Fraction | 28/48 Fraction |
| Mechanical Softwood Pulps | 96 | 0.1 to 0.2 | 0.2 to 0.65 |
| Chemi-mechanical Pulps from Softwood | 84–88 | 0.55 to 1.2 | 0.5 to 0.95 |
| Bleached Softwood Kraft (unbeaten) | 45 | 1.1 to 1.3 | 1.1 |
| Bleached Hardwood Kraft (unbeaten) | 45 | — | 1.2 |
| Unbleached Softwood Bisulphite | 60–70 | 1.5 to 1.7 | — |

EXAMPLE 2

The relationship between the flexibility index as determined by $C_p/C_f$ and fibre flexibility was further indicated by tests carried out using the preferred embodiment of the present invention on bleached softwood kraft pulp samples that had been subjected to various degrees of beating. The results are shown in FIG. 8 as a function of freeness of the whole pulp. (The circles represent the pass 14 retained 28 fraction and the triangles the pass 28 retained 48 fraction of the Bauer-McNatt Classifier). The bleached softwood kraft tested showed clearly that the more the fibre was beaten the greater the flexibility index. Similar tests were carried out on refiner softwood pulp for the fraction retained on a 35 mesh screen i.e. the long fibre fraction at different specific retaining energies. Again, a clear indication of increasing flexibility with increasing energy application is shown in FIG. 9.

EXAMPLE 3

Fibre flexibility is related to fibre conformability as measured by the bulk (or density) of laboratory handsheets decreasing as the bulk increases. It is also known that the bonding of fibres, as manifested by the tensile strength, increases with increasing flexibility through an increase in the relative bonded area of the fibres. FIG. 10 shows examples of mechanical pulps (closed symbols) and chemi-mechanical pulps (open symbols), in which increased fibre flexibility corresponded with an increase in tensile and a decrease in bulk, further indicating that the flexibility index represents fibre flexibility.

EXAMPLE 4

FIG. 11 shows the relationship of the flexibility index with strength properties, and bulk of a thermomechanical pulp (TMP) and a bleached sulphate pulp (Kraft) and their mixtures. It is seen that as the flexibility index increases tensile, burst, and tear increases whereas bulk decreases. Table 2 indicates what the symbols used in FIG. 11 represent.

TABLE 2

| FRACTION | TMP | TMP/KRAFT | KRAFT |
|---|---|---|---|
| Pass 14 Retain 28 | ● | ◐ | ○ |
| Pass 28 Retain 48 | ■ | ◨ | □ |

The ratio of $C_p/C_f$ and $F_p/F_f$ have both been used to designate fibre flexibility, since it has been found that both are indicative of the flexibility of the fibres i.e. there is a specific relationship between these ratios. However, $C_p$ and $C_f$ are not only the more easily obtained values but also provide larger scale differences (see FIG. 6) and as above indicated, it is preferred to use these values to designate the flexibility index.

Modifications may be made without departing from the spirit of the invention as defined in the appended claims.

I claim:

1. A method for measuring the fibre flexibility of fibres comprising; screening slurry of said fibres to obtain a feed fraction having a preselected average fibre length, adjusting the consistency of the feed fraction to a selected consistency in the range of 0.05 to 0.3%, spraying said feed fraction against the bottom of a substantially horizontal screen having openings the minimum dimensions of which are substantially equivalent to a b/L ratio of 0.3 to 0.7 for a square opening screen, wherein b equals the dimension of one side of the square opening and L equals the average fibre length of the feed fraction, maintaining a negative pressure in above said horizontal screen sufficient so as to obtain a flow of slurry through said screen but without the formation of a mat beneath said screen and to divide said feed fraction into a retained and a pass fraction, obtaining a ratio indicative of a mass of fibres in the pass or retained fraction to the mass of fibres in said feed, thereby to obtain an indication of the flexibility of the fibres.

2. A method as defined in claim 1 wherein said consistency is about 0.15%.

3. A method as defined in claim 1 wherein said b/L ratio is between 0.5 and 0.6.

4. A method as defined in claims 1, 2 or 3 wherein said negative is in the "stabilized" flow region.

5. A method as defined in claims 1, 2 or 3 wherein a pressure drop across said screen of 20 to 25 mm of $H_2O$ is maintained.

6. A method as defined in claims 1, 2 or 3 wherein said spraying comprise spraying said feed fraction in a manner so that the orientation of the fibres striking the bottom of said screen is random.

7. An apparatus for measuring the fibre flexibility comprising, a substantially horizontal screen an upper housing communicating with the top of said screen, means for spraying a feed slurry of fibres to be tested with said fibres in random orientation onto the bottom of said horizontal screen, means for maintaining a negative pressure in said upper housing to obtain flow of a passed slurry through said screen without the formation of a mat on the bottom of said screen and divide said feed slurry into a passed and a retained fraction, means for removing said passed fraction from said upper housing whereby a radio indicative of the fibres in said passed or retained fraction to the mass of fibres in said feed slurry may be obtained.

8. An apparatus as defined in claim 7 further comprising a first container and a second container and first and second screening means, said first screening means having openings larger than said second screening means, means for pumping a slurry from said first chamber to first screening means thereby to separate said sample into a retained fraction and a pass fraction, collecting said pass fraction in said second chamber, means for pumping said pass fraction from said second chamber to said second screening means to form a second pass and a second retained fraction, means for conducting said second retained fraction to said second chamber, and means for connecting said first or said second chamber to said nozzle means to direct a pulp fraction accumulated in said first or said second chamber selectively against the bottom of said horizontal screen.

* * * * *